(12) United States Patent
Eversmann et al.

(10) Patent No.: US 7,662,341 B2
(45) Date of Patent: Feb. 16, 2010

(54) SENSOR ARRANGEMENT AND METHOD FOR OPERATING A SENSOR ARRANGEMENT

(75) Inventors: Björn-Oliver Eversmann, München (DE); Christian Paulus, Weilheim (DE); Roland Thewes, Gröbenzell (DE)

(73) Assignee: Infineon Technologies AG, Munich (DE)

( * ) Notice: Subject to any disclaimer, the term of this patent is extended or adjusted under 35 U.S.C. 154(b) by 672 days.

(21) Appl. No.: 10/530,882

(22) PCT Filed: Oct. 14, 2003

(86) PCT No.: PCT/EP03/11381

§ 371 (c)(1),
(2), (4) Date: Apr. 11, 2005

(87) PCT Pub. No.: WO2004/036203

PCT Pub. Date: Apr. 29, 2004

(65) Prior Publication Data

US 2006/0057025 A1    Mar. 16, 2006

(30) Foreign Application Priority Data

Oct. 14, 2002    (DE) ............................. 102 47 889

(51) Int. Cl.
*G01N 33/00* (2006.01)
(52) U.S. Cl. .................. 422/82.02; 422/50; 422/82.01; 422/99
(58) Field of Classification Search .................. 422/50, 422/82.01, 82.02, 99
See application file for complete search history.

(56) References Cited

U.S. PATENT DOCUMENTS 4,322,680 A    3/1982    Janata (Continued)

FOREIGN PATENT DOCUMENTS

DE    101 51 020 A1    4/2003

(Continued)

OTHER PUBLICATIONS

Nenad Stevanovic, Mathias Hillebrand, Bedrich J. Hosticka and Andreas Teuner, *A CMOS Image Sensor for High-Speed Imaging*, 2000 IEEE International Solid-States Circuits Conference, 2000.

(Continued)

*Primary Examiner*—Sam P Siefke
(74) *Attorney, Agent, or Firm*—Brinks Hofer Gilson & Lione

(57) ABSTRACT

A sensor arrangement and method of operating the sensor arrangement are described. The sensor arrangement has sensor devices formed on or in a substrate and a calibration device for calibrating a respective sensor device. Each sensor device has an electrical signal converter which is a field-effect transistor (FET) having a gate terminal coupled to a sensor element that is coupled to the signal converter, a device that keeps constant the electrical voltage between source and drain terminals of the FET, and a device for detecting the value of the electric current flowing through the signal converter. The sensor element characteristically influences the electrical conductivity of the signal converter on account of a sensor event on the sensor element. The calibration device brings the gate region of the FET to an electrical calibration potential such that the electric current is independent of parameter fluctuations of the FET.

12 Claims, 6 Drawing Sheets

U.S. PATENT DOCUMENTS

Figure 1:
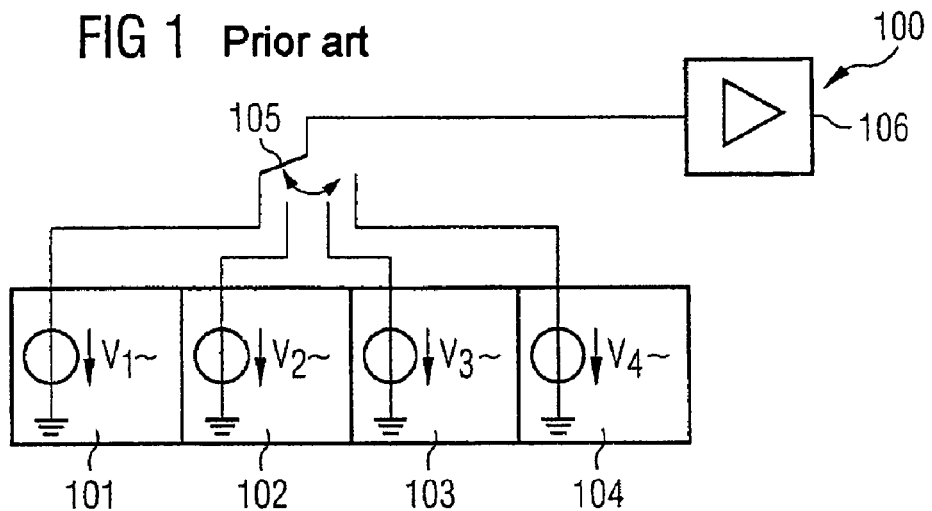

| | | |
|---|---|---|
| 4,411,741 A | 10/1983 | Janata |
| 4,514,263 A | 4/1985 | Janata |
| 6,011,251 A | 1/2000 | Dierickx et al. |
| 6,181,194 B1 | 1/2001 | Tiilikainen |
| 6,321,588 B1 | 11/2001 | Bowers et al. |
| 6,922,081 B2 | 7/2005 | Frey et al. |
| 2001/0044177 A1 | 11/2001 | Fukushima et al. |
| 2005/0017190 A1 | 1/2005 | Eversmann et al. |

FOREIGN PATENT DOCUMENTS

| | | |
|---|---|---|
| EP | 0 241 991 A2 | 10/1987 |
| FR | 2779826 | 12/1999 |
| JP | 58-129239 | 8/1983 |
| JP | 11-186909 | 7/1999 |
| JP | 2000-55874 | 2/2000 |
| JP | 2000-152088 | 5/2000 |
| JP | 2002-195997 | 7/2002 |
| WO | WO 88/08972 | 11/1988 |
| WO | WO 99/66319 | 12/1999 |
| WO | WO 02/33397 A1 | 4/2002 |
| WO | WO 03/038420 A1 | 5/2003 |

OTHER PUBLICATIONS

International Search Report from corresponding International Application No. PCT/EP03/11381, Oct. 3, 2004.
Preliminary Examination Report from corresponding International Application No. PCT/EP03/11381, Jun. 28, 2004.
Japanese Office Action Dated Jan. 16, 2008.
Japanese Office Action Dated Mar. 18, 2009.

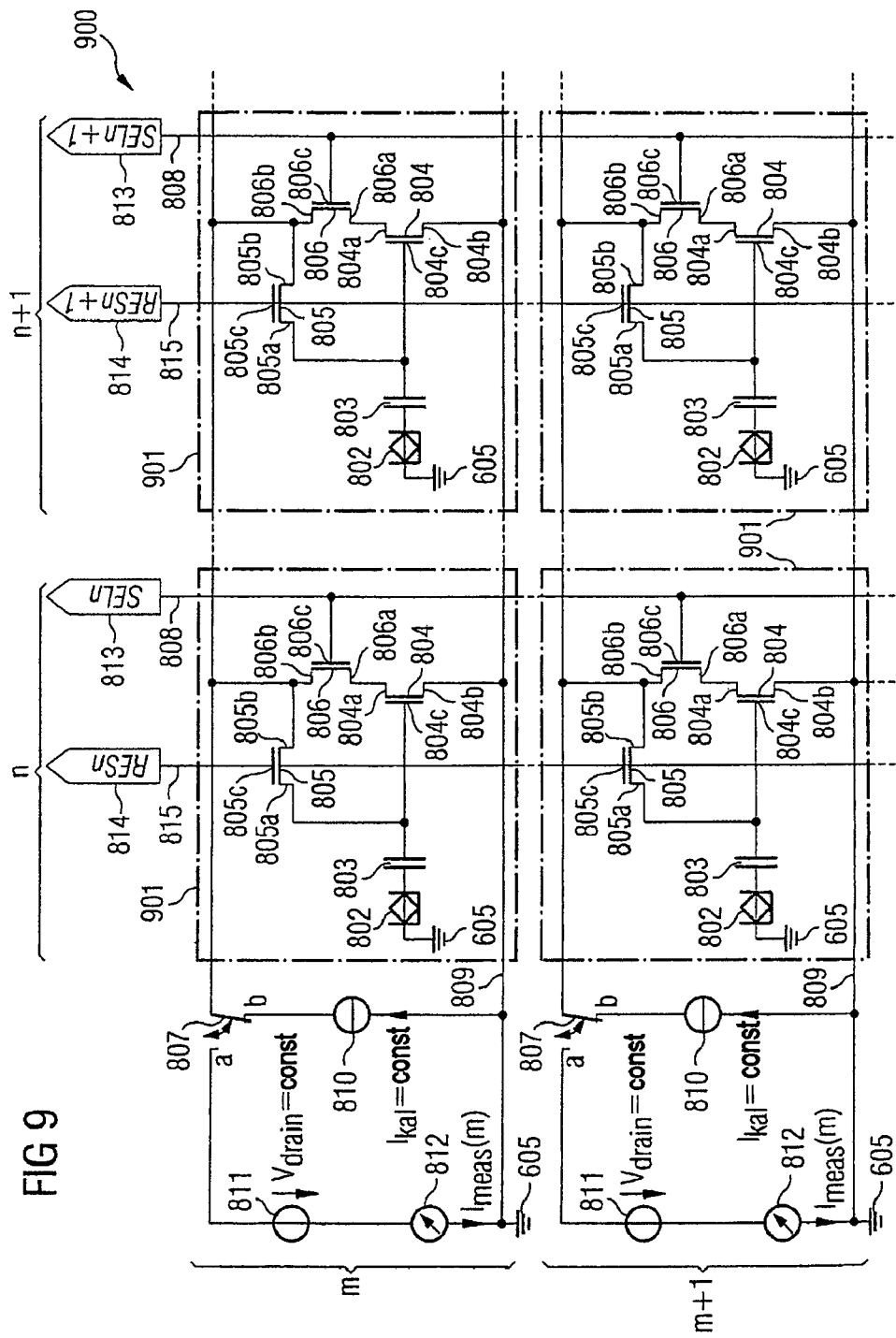

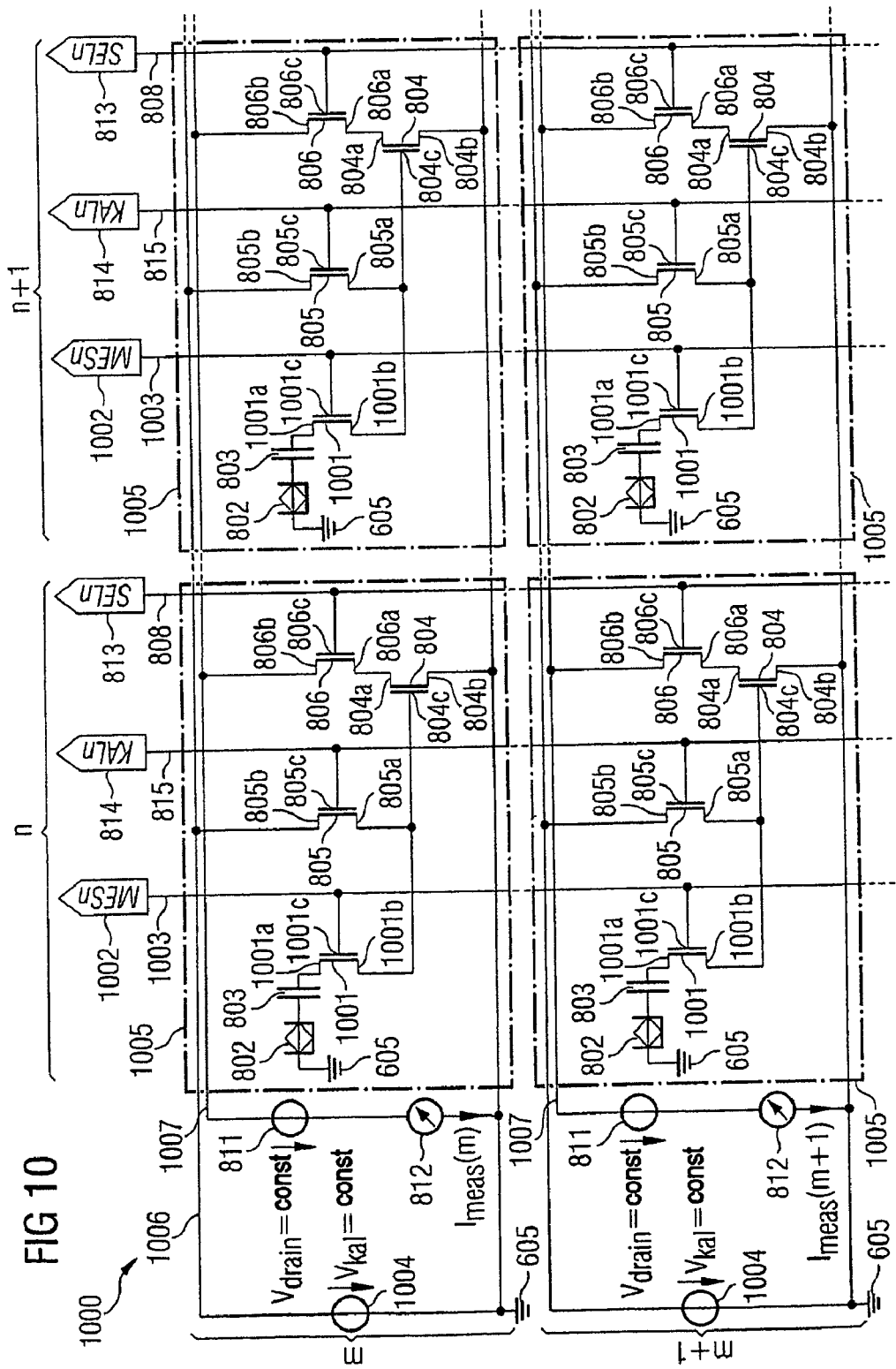

SENSOR ARRANGEMENT AND METHOD FOR OPERATING A SENSOR ARRANGEMENT

This application is the national stage application of international application number PCT/EP2003/011381, filed on Oct. 14, 2003, which claims the benefit of priority to German Patent Application 102 47 889.9, filed on Oct. 14, 2002, herein incorporated herein by reference.

The invention relates to a sensor arrangement and a method for operating a sensor arrangement.

The interface between biology and semiconductor technology is of interest from scientific and economic standpoints. Mention may be made in this connection of, by way of example, the coupling between biological cell assemblages, such as neurons for example, and silicon microelectronics. A biological system may be examined in spatially or temporally resolved fashion on the surface of a semiconductor-technological sensor by means of sensor elements arranged in matrix form. In particular, metabolism parameters of the cells can be recorded for example by detecting local pH values with the aid of ion-sensitive field-effect transistors (ISFETs) as sensor elements. An ISFET has an ion-sensitive layer in operative contact with electrically charged particles to be detected, the electrically charged particles characteristically influencing the conductivity of the ISFET, which can be detected as a sensor variable.

Examining the reaction of a biological system to an electrical stimulation is of great interest. Neurons (nerve cells) can generate a small electric current via ion channels in the cell membranes in specific regions of their surface, said current being detected by a sensor situated underneath. The requisite stringent requirements made of spatial and temporal resolution of the sensor are achieved by means of silicon microelectronics.

Matrix-type arrangements of sensor elements are also used in other important fields such as medical analysis or DNA sensor technology.

For these and other possible applications of semiconductor sensors in integrated circuits, it is advantageous to integrate a large number of sensors in a common sensor array. Even in the case of small sensor arrays (and all the more so in the case of large sensor arrays), not every sensor can be connected to a dedicated read-out circuit. The number of requisite lines and also the redundancy of the read-out circuits arranged outside the array are factors opposing such a solution.

FIG. 1 schematically shows a sensor arrangement 100 in accordance with the prior art having four sensor devices 101 to 104, a multiplexer represented as switch 105, and a read-out circuit 106.

The outputs of the individual sensor devices are read out using the multiplexer 105, that is to say serially. The respective sensor device 101 to 104 coupled to the read-out circuit 106 via the multiplexer 105 outputs an output voltage correlated with the event to be detected (for example the illumination intensity in the case of a photosensor or an electrical signal of a nerve cell arranged on the respective sensor device). In order to represent these facts schematically, the sensor devices 101 to 104 are represented schematically as voltage sources $V_1, V_2, V_3, V_4$.

In accordance with the scenario illustrated in FIG. 1, the first sensor device 101 is coupled to the read-out circuit 106 via the multiplexer 105. By means of the read-out circuit 106, the output voltage of a respective sensor device 101 to 104 is amplified for further processing.

If it is necessary to record the measured values of a multiplicity of sensor devices with a high sampling rate, then an individual sensor device has to be read in a very short time. This results in a stringent requirement made of the temporal resolution of the system.

Figure 2:
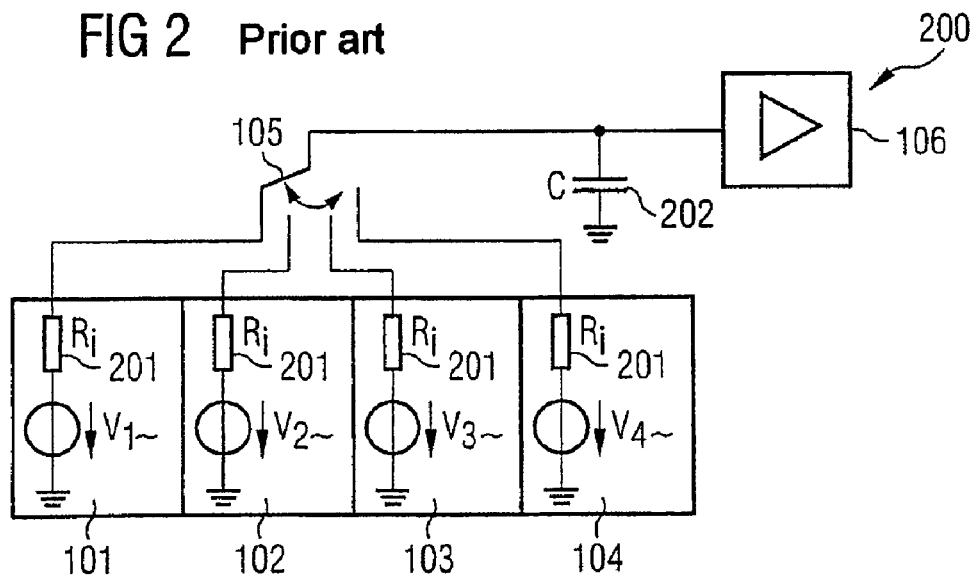

The sensor arrangement 200 in accordance with the prior art as shown in FIG. 2 exhibits, in addition to the components described in FIG. 1, an internal resistance $R_i$ 201 of each of the sensor devices and also a common capacitance C 202 of the sensor devices 101 to 104. The time constant of the sensor arrangement 200 is determined by means of the RC element comprising internal resistance $R_i$ of the sensor devices 101 to 104 and also the capacitance C 202 that is to be subjected to charge reversal. These two parameters are subject to specific limitations for a specific production technology. Consequently, the achievable time constant $\tau=RC$ is also limited.

The time constant $\tau$ clearly specifies the time after which the output signal has risen to $(1-1/e)=63\%$ of the final value. If measurement errors caused by the transient response of the sensor arrangement 200 are intended to lie below a specific, just still tolerable limit, it is necessary, under certain circumstances, to wait during multiples of these time constants (e.g. $2\tau$ or $3\tau$). Consequently, the time constant $\tau=RC$ is a characteristic measure of the minimum time that can be attained between two successive measurements. Therefore, the value of $\tau$ results in a limitation of the maximum number of sensor devices that can be read within a predetermined time segment at a predetermined sampling rate.

Figure 3:
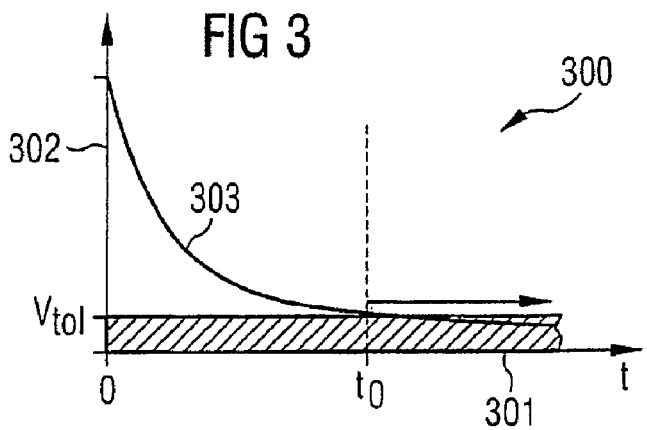

FIG. 3 is a diagram 300 schematically showing the time dependence of the signal profile at a sensor device 201 to 204 after the production of the coupling (t=0) of the respective sensor device to the read-out circuit 106 via the multiplexer 105.

The time that has elapsed since the changeover of the multiplexer 105 (t=0) is plotted along the abscissa 301 of the diagram 300. At the instant $t_0$, the signal profile has for the first time fallen below the predetermined tolerable value $V_{tol}$. The temporal signal profile at the voltage sources $V_1$ to $V_4$ represented schematically in FIG. 1, FIG. 2, is represented along the ordinate 302 of the diagram 300. The signal profile curve 303 reflects the transient response at the capacitance 202 and the resistances $R_i$, and to a good approximation is a falling exponential function. Clearly, at the instant $t_0$, the dynamic error has for the first time fallen below the tolerable error, so that the measurement time that is necessary at the least is $t_0$.

In the case of sensor arrangements disclosed in the prior art, the sensor devices of a sensor array are read in the voltage domain, that is to say that the measurement variable is converted into an electrical voltage. In order to keep down the RC constant, and therefore to enable sufficiently many sensor devices to be read sufficiently rapidly, attempts are made to reduce the internal resistance $R_i$ and, as a consequence thereof, the time constant $\tau$.

One possibility for reducing the internal resistance $R_i$ of the sensor devices independently of the circuit architecture is to increase the driver capability of the output transistors of a circuit. The disadvantage of this measure is an increased area requirement and a greater capacitive loading on the preceding amplifier stage or the connected sensor, which leads to an attenuation of the signal. On account of the frequently severe area limitation and the need for efficient area utilization, this solution is not suitable for many fields of application.

Usually, for integrated circuits operated in the voltage domain, a series of basic circuits are used for the output drivers. What is disadvantageous about an additional output driver circuit integrated into the sensor devices is the increase in the space requirement of a sensor device and, consequently, the reduction of the achievable spatial resolution. A boundary condition for the consideration below is that an output transistor coupled to a sensor electrode is simultaneously used for signal amplification. This is not a mandatory prerequisite, however.

Figure 4A:
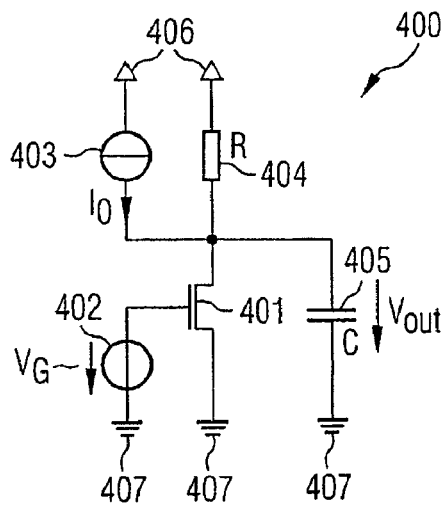

FIG. 4A illustrates an output driver circuit 400, in the case of which a MOS transistor 401 is operated in a common-source connection.

The sensor device is represented as voltage source $V_G$ 402. Furthermore, the output driver circuit 400 is shown with a constant-current source $I_0$ 403, a nonreactive resistance R 404 representing the internal resistance of the sensor device, and also a capacitance C 405 representing the capacitance of a sensor arrangement. The output voltage $V_{out}$ is present across the capacitance 405. The voltage source 402 is coupled to the gate terminal of a MOS transistor 401. One source/drain terminal of the MOS transistor 401 is at ground potential 407, whereas the other source/drain terminal of the MOS transistor 401 is coupled both to the constant-current source 403 and to the nonreactive resistance 404 and to the capacitance 405. The operating point of the MOS transistor 401 is determined by means of the constant-current source 403, the nonreactive resistance 404 and the voltage source $V_G$ 402.

Figure 4B:
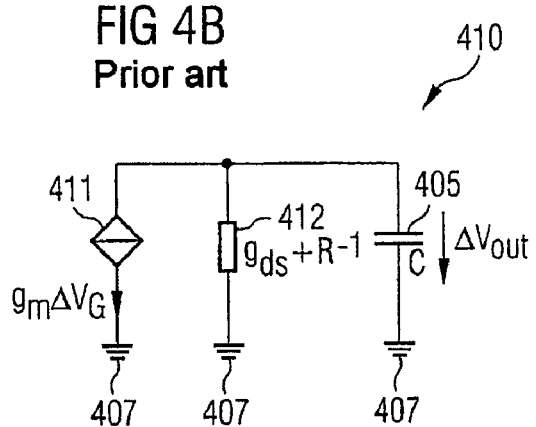

FIG. 4B shows a small-signal equivalent circuit diagram 410 of the output driver circuit 400 shown in FIG. 4A. The equivalent circuit diagram 410 shows a controlled current source 411 ($g_m \Delta V_G$), an effective internal resistance 412 $(g_{ds}+R^{-1})^{-1}$ and also the capacitance 405 that is to be subjected to charge reversal. $g_{ds}$ designates the output conductance of the MOS transistor 401, and $g_m$ is the transconductance of the MOS transistor 401.

In the case of the common-source connection of the MOS transistor 401 as shown in FIG. 4A, FIG. 4B, one source/drain terminal is at ground potential 407. The operating point of the output driver circuit 400 is predetermined by means of the DC component of the voltage source $V_G$ 402 at the gate terminal of the MOS transistor 401 and by means of the constant-current source $I_0$ with the internal resistance R coupled to the other source/drain terminal of the MOS transistor 401. A solution without a constant-current source $I_0$ 403, just with a nonreactive resistance R 404, is also possible as an alternative. In the case of the output driver circuit 400 shown in FIG. 4B, a supply voltage 406 is applied to a respective terminal of the constant-current source 403 and of the nonreactive resistance 404, whereas a terminal of the voltage source 402, one source/drain terminal of the MOS transistor 401 and a terminal of the capacitance 405 are at ground potential 407.

If the gate voltage $V_G$ is modulated (for example on account of a sensor event), then the drain current $I_D$ of the MOS transistor 401 changes by $g_m \Delta V_G$. This is symbolized by means of the controlled current source 411 from FIG. 4B, showing the small-signal equivalent circuit diagram of the output driver circuit 400. The change in the output voltage $\Delta V_{out}$ results from the changed voltage drop across the MOS transistor 401 and across the effective resistance 412. For low frequencies ω, the capacitance C can be disregarded to a good approximation, and this results in an open-loop gain A(ω=0) which can be described by means of the following expression:

$$A(\omega=0)=\Delta V_{out}/\Delta V_G=g_m/(g_{ds}+R^{-1}) \quad (1)$$

If transistor parameters that are typical of CMOS technology are inserted into equation (1), this results in a possible voltage gain by a factor of approximately ten to approximately fifty. As a result, even signals having a small amplitude are amplified after the first amplifier stage such that they are no longer appreciably disturbed by noise effects. The time constant $\tau_c$ of the amplifier results as:

$$\tau_c=C/(g_{ds}+R^{-1}) \quad (2)$$

The capacitance is predetermined by the technology used and, in this respect, can only be influenced to a very limited extent, for example by means of optimizing the layout. The parameters R and $g_{ds}$ cannot be varied arbitrarily for a specific gain and on account of area limitations, so that a limit value for the maximum bandwidth that can be transmitted results from these boundary conditions.

Figure 5A:
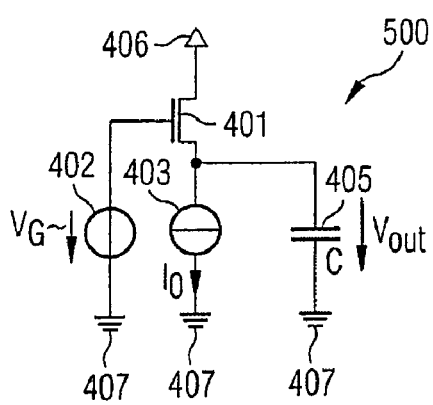

A description is given below, referring to FIG. 5A, of a further output driver circuit 500 in accordance with the prior art. An equivalent circuit diagram 510 of the output driver circuit 500 shown in FIG. 5A is described referring to FIG. 5B. Those components of the output driver circuit 500 which are also contained in the output driver circuit 400 are provided with the same reference numerals.

In the case of the output driver circuit 500 shown in FIG. 5A, the MOS transistor 401 is configured in a source follower connection. In a departure from the output driver circuit 400 shown in FIG. 4A, that source/drain terminal of the MOS transistor 401 which is not coupled to the constant-current source 403, the voltage source 402 and the capacitance 405 is at the potential of the supply voltage 406. Furthermore, a terminal of the constant-current source 403 and a terminal of the capacitance 405 are at the electrical ground potential 407 in the case of the output driver circuit 500. The constant-current source $I_0$ 403 and the voltage source $V_G$ 402 determine the operating point of the MOS transistor 401.

The electric current at the source/drain terminal of the MOS transistor 401 that is coupled to the constant-current source $I_0$ 403 is determined by means of the constant-current source $I_0$ 403. The gate voltage of the MOS transistor 401 is set by means of the voltage source $V_G$ 402. Furthermore, a capacitance C 405 that is to be subjected to charge reversal is shown.

Figure 5B:
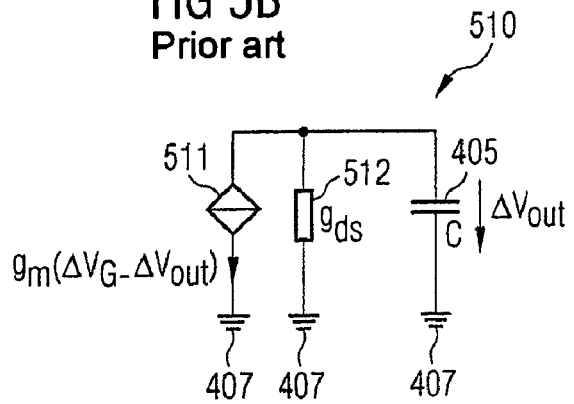

The small-signal equivalent circuit diagram 510 of FIG. 5B shows a controlled current source $g_m(\Delta V_G - \Delta V_{out})$ 511 and also an internal resistance $g_{ds}$. In accordance with the small-signal equivalent circuit diagram 510 shown in FIG. 5B, the field-effect-based modulation of the electric current at the lower source/drain terminal of the MOS transistor 401 in accordance with FIG. 5A is represented as controlled current source $g_m(\Delta V_G - V_{out})$ 511.

The dependence of said electric current on the electrical voltage at the lower source/drain terminal of the MOS transistor 401 in accordance with FIG. 5A is determined by the conductance $g_{ds}$. The time constant $\tau_c$ of the amplifier is determined by the RC element and is described by the following expression:

$$\tau_c=C/(g_{ds}+g_m) \quad (3)$$

The time constant $\tau_c$ from equation (3) corresponds to the scenario of the common-source connection of the MOS transistor 401 from FIG. 4A if the value of the nonreactive resistance R is equal to the inverse transconductance $g_m^{-1}$ of the MOS transistor 401 (cf. equation (2)). In accordance with the two circuit architectures, the gain is then approximately one, namely:

$$A(\omega=0)=\Delta V_{out}/\Delta V_G=g_m/(g_m+g_{ds})\leq 1 \quad (4)$$

This low gain is disadvantageous, on account of the small signal amplitudes that have to be conducted out from the sensor device, since noise effects can corrupt the measured signal.

An example of a realization of the principle described on the basis of a CMOS camera, in "A CMOS Image Sensor for High-Speed Imaging", IEEE International Solid-State Circuits Conference 2000:104-105, N. Stevanovic, M. Hillebrand. B. J. Hosticka, A. Teuner (2000).

To summarize, the functionality of the circuit architectures disclosed in the prior art for reading out sensor signals of a sensor array is inadequate since a large time constant for reading the individual sensor devices results from the capacitance that is to be subjected to charge reversal. This leads to a poor temporal resolution. Furthermore, the gain of the often small sensor signal is often insufficient in the case of circuit architectures disclosed in the prior art.

The invention is based on the problem of providing a sensor arrangement having high spatial resolution which, in conjunction with a sufficiently high signal gain, enables a fast read-out of sensor signals, i.e. a high bandwidth.

The sensor arrangement according to the invention contains a plurality of sensor devices formed on and/or in a substrate. Each sensor device has an electrical signal converter and a sensor element coupled to the signal converter, which sensor element can be used to characteristically influence the electrical conductivity of the signal converter on account of a sensor event on the sensor element. Furthermore, the sensor device according to the invention has a device for keeping constant an electrical voltage present at the signal converter. Moreover, each sensor device has a device for detecting the value of the electric current flowing through the signal converter as sensor signal.

Furthermore, the invention provides a method for operating a sensor arrangement having the features mentioned above, in which case, in accordance with the method, the electrical conductivity of the signal converter is characteristically influenced on account of a sensor event on a respective sensor element. Furthermore, the electrical voltage at the signal converter is kept constant. The electric current flowing through the signal converter is detected as sensor signal.

A fundamental idea of the invention is based on detecting, instead of the electrical voltage, an electric current at a signal converter coupled to the sensor element. By virtue of an electric current being detected according to the invention, rather than an electrical voltage in accordance with the prior art, a charge reversal of capacitances is avoided. A larger bandwidth, that is to say a faster read-out of the sensor elements of a sensor arrangement, is made possible as a result. The time constant of the system is no longer defined by the interconnection within the sensor device, but rather only by the external circuit. Clearly, the electrical voltage as sensor signal is stabilized externally according to the invention. With the circuit architecture according to the invention for a sensor arrangement, a particularly high number of sensor elements and a particularly high sampling rate are made possible for a predetermined technology, thereby achieving a small time constant for reading the sensor elements. On account of the interconnection of the sensor device according to the invention, an electric sensor current is detected instead of an electrical sensor voltage, which leads to a high gain and a small time delay.

If, instead of the electrical voltage $V_{out}$, the electric current $I_{out}$ is used as output variable of the output stage of a sensor device or of the signal converter, then the voltage across the capacitance becomes independent of the output variable and can be kept constant at a value of the output voltage, by way of example. Since the inductive properties of integrated leads are generally negligible compared with the capacitive properties, this results in a considerably reduced time constant. In practice, an unavoidable internal resistance of the measuring circuit leads to a small voltage drop. However, since the measuring circuit is situated outside the sensor devices, its internal resistance can be kept down. As a result, the time constant $\tau=RC$ is orders of magnitude smaller than in accordance with the prior art. Sensor arrangements that can be read faster or an increased number of sensor devices are made possible as a result.

Clearly, an output driver circuit of a sensor device is embodied in a "current mode technology".

A further important aspect of the invention is to be seen in the fact that a plurality of sensor devices are formed on and/or in the substrate. In other words, the sensor arrangement according to the invention is realized as an integrated circuit, for example in and/or on a silicon substrate (e.g. wafer, chip, etc.). Miniaturization is achieved as a result and an array having a high number of sensor devices is thus produced. Furthermore, the sensor arrangement can be fabricated with tenable outlay using the modern and mature silicon microtechnology.

In the case of the sensor arrangement, the electronic signal converter is preferably a transistor (e.g. a bipolar transistor).

In at least some of the sensor devices according to the invention, the electronic signal converter may be a field-effect transistor whose gate terminal is coupled to the sensor element, the device for keeping constant an electrical voltage being set up in such a way that it keeps constant the electrical voltage between the source/drain terminals of the field-effect transistor. A field-effect transistor as signal converter has the functionality that a modulation of the gate voltage is converted into an altered electrical conductivity of the channel region of the field-effect transistor, so that the value of the electric current flowing through a source/drain terminal is characteristically influenced on account of the altered nonreactive resistance of the channel region of the field-effect transistor.

As an alternative to a field-effect transistor, the electronic signal converter may be embodied as an arbitrarily configured controllable nonreactive resistor, for example as a potentiometer, the resistance of which is controlled for example by means of an electrical signal on account of a sensor event.

Furthermore, the sensor device according to the invention may have an evaluation unit, the evaluation unit being provided with the value of the electric current as sensor signal.

The evaluation unit is preferably set up in such a way that it forms, from the value of the electric current, an electrical voltage characteristic of this value or maps the value of the electric current onto a digitally coded value that characterizes the latter.

In other words, the detected electric current can be converted into an electrical voltage, which may be advantageous for the further processing of the signal. Furthermore, an analog current signal can be converted into a digital signal—and hence a signal that is more robust in respect of errors.

In particular, the evaluation unit may have an operational amplifier, in particular connected up as a voltage follower, having a first input, to which the sensor signal can be applied. Furthermore, the operational amplifier has a second input, to which an electrical reference potential can be applied. The characteristic electrical voltage is provided at an output of the operational amplifier, the first input and the output being coupled to one another by means of a nonreactive resistor.

The sensor arrangement may be configured as a biosensor arrangement. The sensor element of each sensor device may for example detect an electrical signal of a nerve cell grown on the sensor element. As an alternative, the sensor element may detect electrically charged particles on the sensor element-using an ISFET.

The sensor arrangement may have a calibration device for calibrating a respective sensor device, which is set up in such a way that it can be used to bring the gate region of the field-effect transistor to an electrical calibration potential such that the electric current is independent of parameter fluctuations of the field-effect transistor. By way of example, field-effect transistors of different sensor devices may have different parameters (e.g. threshold voltage) due to a fabrication method. The calibration makes it possible to ensure that parameter fluctuations do not lead to corruption in the detection of a sensor event.

In particular, the sensor device can be calibrated by means of implementing a calibration device based on the autozeroing technique, thereby providing a robust sensor arrangement. A signal influencing on account of parameter fluctuations of the components of a respective sensor device, for example the signal converters realized as field-effect transistors, is thereby avoided.

The calibration device may be set up in such a way that an electric calibration current can be applied to the gate terminal and to a source/drain terminal of the field-effect transistor for calibration purposes.

As an alternative, the evaluation unit may have a correlated double sampling device, which may be set up in such a way that it forms, in the case of a sensor event, a value of the electric current that is independent of parameter fluctuations of a respective field-effect transistor.

In accordance with the correlated double sampling principle, clearly in a first step a sensor event is detected in a sensor device and the sensor signal is stored. This sensor signal is dependent on the alteration of the value of the physical parameters of the sensor device (for example geometrical parameters of a field-effect transistor) and may furthermore be dependent on physical parameters of further components, for example an amplifier for amplifying the sensor signal. In a second step, an auxiliary signal that depends only on the value of the physical parameter of the sensor device is detected in the absence of a sensor event. If the auxiliary signal is subtracted from the sensor signal, then a sensor signal that is essentially independent of the value of the physical parameter is obtained.

In particular, the correlated double sampling device of the invention may be set up in such a way that, by means of this device, in a calibration phase, the gate region of the field-effect transistor is brought to an electrical calibration potential and the associated value of the electric current is detected as calibration signal and stored. In a detection phase, the value of the electric current on account of a sensor event is detected as sensor signal. In an evaluation phase, sensor signal and calibration signal can be evaluated jointly.

Preferably, the sensor devices of the sensor arrangement are arranged essentially in matrix form on and/or in the substrate and are connected up by means of row and column lines in such a way that the sensor devices can be driven individually, row by row or column by column.

In the case of the sensor arrangement according to the invention, at least one evaluation unit, at least one calibration device and/or at least one correlated double sampling device may be provided jointly for at least a portion of the sensor devices of a row line or a column line.

The method according to the invention for operating the sensor arrangement according to the invention is described in more detail below. Refinements of the sensor arrangement are also applicable to the method for operating the sensor arrangement, and vice versa.

In accordance with the method according to the invention, a field-effect transistor whose gate terminal is coupled to the sensor element may be used as the electronic signal converter of a respective sensor arrangement, the electrical voltage between the source/drain terminals of the field-effect transistor being kept constant by means of the device for keeping constant an electrical voltage.

Furthermore, a respective sensor device may be calibrated by the gate region of the field-effect transistor being brought to an electrical calibration potential such that the value of the electric current in the case of a sensor event becomes independent of the properties of the field-effect transistor (e.g. a production-dictated deviation of the thickness of the gate insulating layer from a desired or average value).

A value of the electric current that is independent of the properties of the field-effect transistor may be formed using the correlated double sampling method in the case of a sensor event.

Exemplary embodiments of the invention are illustrated in the figures and are explained in more detail below.

Figure 6:
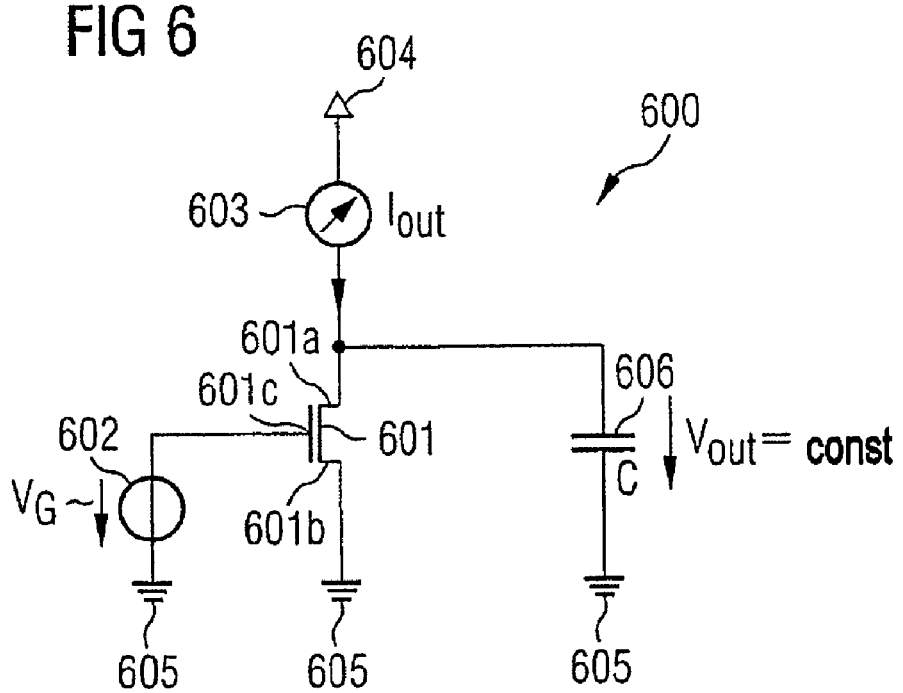
Figure 7:
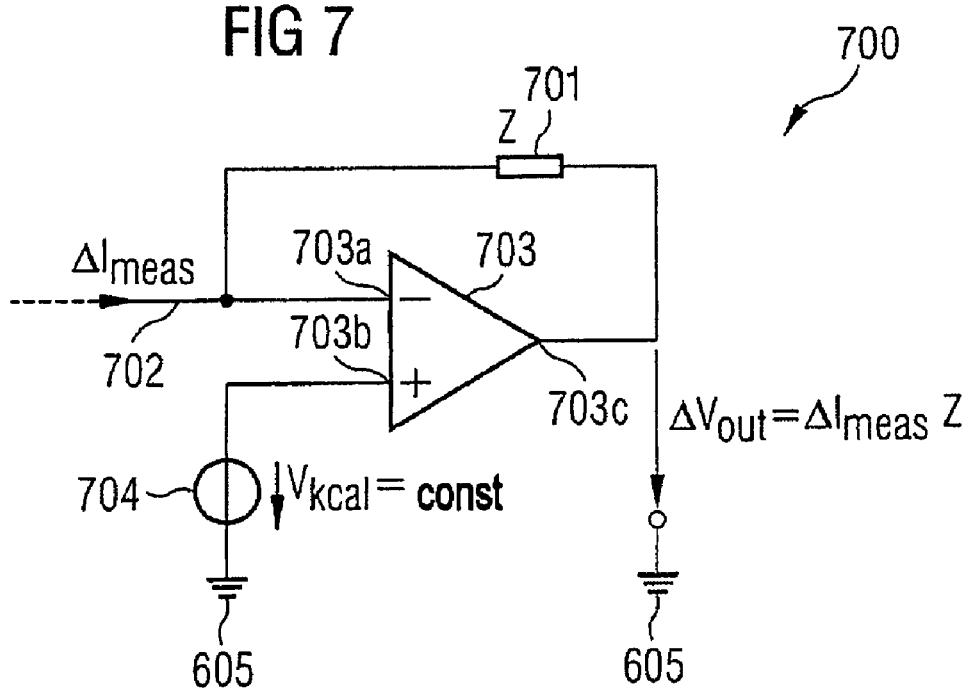
Figure 8:
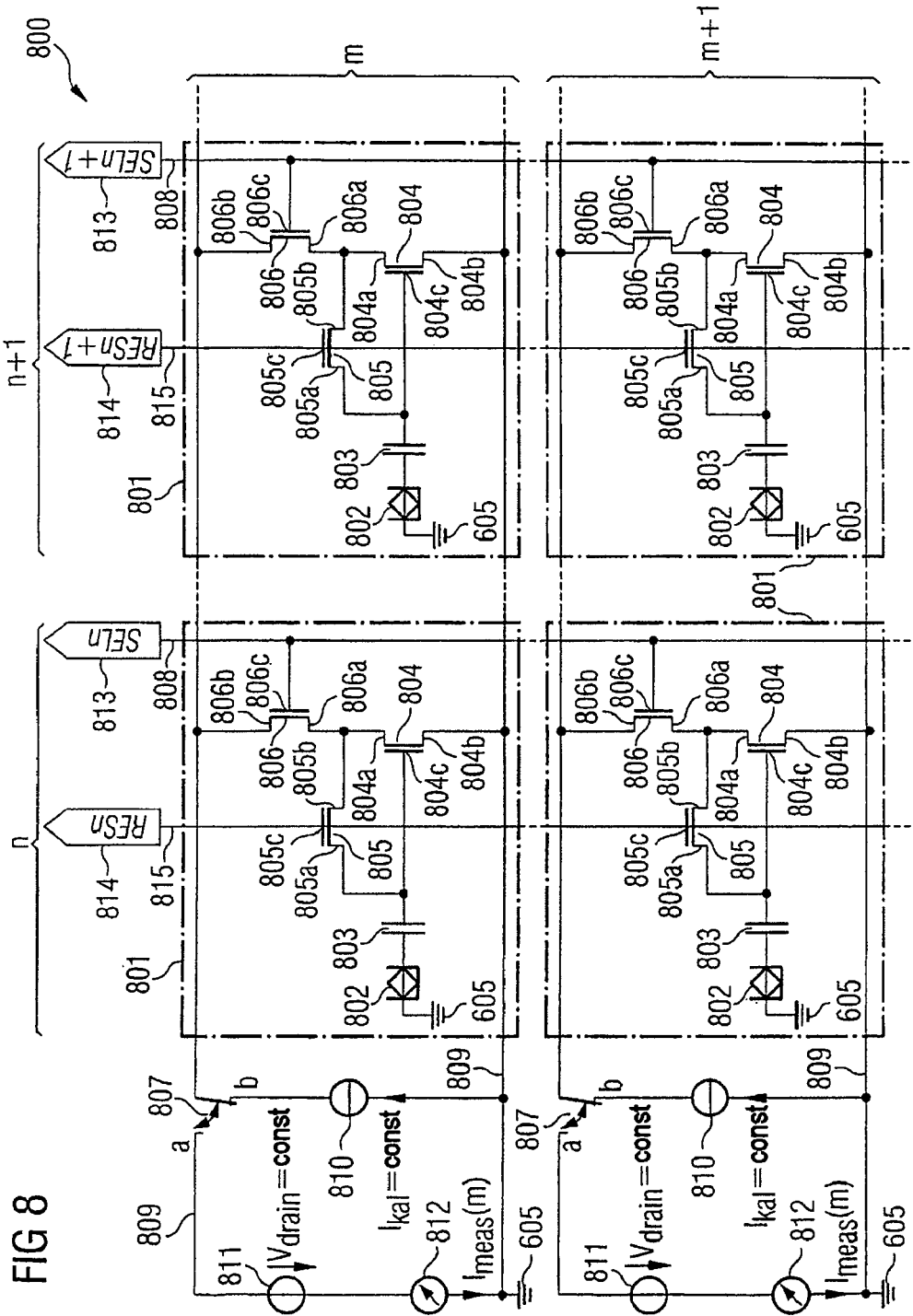

In the figures:

FIG. 1 shows an illustration of one sensor arrangement in accordance with the prior art, FIG. 2 shows an illustration of another sensor arrangement in accordance with the prior art, FIG. 3 shows a diagram illustrating a signal profile as a function of a read-out time, FIG. 4A, FIG. 4B show one output driver circuit and an associated small-signal equivalent circuit diagram in accordance with the prior art, FIG. 5A, FIG. 5B show another output driver circuit and an associated small-signal equivalent circuit diagram in accordance with the prior art, FIG. 6 shows a sensor device in accordance with a preferred exemplary embodiment of the invention, FIG. 7 shows an evaluation unit according to the invention, FIG. 8 shows a sensor arrangement in accordance with a first exemplary embodiment of the invention, FIG. 9 shows a sensor arrangement in accordance with a second exemplary embodiment of the invention, FIG. 10 shows a sensor arrangement in accordance with a third exemplary embodiment of the invention.

A description is given below, referring to FIG. 6, of a sensor device 600 in accordance with a preferred exemplary embodiment of the invention.

The sensor device 600 shown in FIG. 6 has a field-effect transistor 601 as electrical signal converter. Furthermore, the sensor device 600 has a biosensor element coupled to the field-effect transistor 601, which biosensor element is represented schematically as voltage source 602 in FIG. 6. If a sensor event takes place at the biosensor element, then the electrical conductivity of the channel region of the field-effect transistor 601 is characteristically influenced on account of said sensor event.

A first source/drain terminal 601a of the field-effect transistor 601 is coupled to one terminal of an ammeter 603 for detecting a sensor current $I_{out}$, a supply voltage 604 being applied to the other terminal of said ammeter. A second source/drain terminal 601b of the field-effect transistor 601 is at the ground potential 605. On account of this interconnection, a constant electrical potential difference is applied between the source/drain terminals 601a, 601b. Furthermore, the constant voltage $V_{out}$, which results from the difference between the supply voltage 604 and the ground potential 605, is also present across a capacitor 606 representing the effective capacitance of the sensor device 600. The ammeter 603 is a device for detecting the value of the electric current flowing through the first source/drain terminal 601a of the field-effect transistor 601 as sensor signal.

The gate terminal 601c of the field-effect transistor 601 is coupled to the voltage source 602. The electrical voltage between the source/drain terminals 601a, 601b of the field-effect transistor 601 is constant. The first source/drain terminal 601a of the field-effect transistor 601 is coupled to one terminal of the capacitor 606 and is furthermore coupled to the ammeter 603.

If a sensor event takes place on the biosensor element, then the electrical voltage $V_G$ of the voltage source 602 is thereby modulated. The latter is provided at the gate terminal 601c of the field-effect transistor 601, so that the electrical conductivity of the channel region of the field-effect transistor 601 is thereby characteristically influenced. As a result, the value of the electric current flow through the source/drain terminal 601a of the field-effect transistor 601, which current flow is detected by the ammeter 603, is a characteristic measure of the sensor event.

The field-effect transistor 601 is operated in the "current mode". The voltage source 602 $V_G$ determines the potential present at the gate region 601c, whereas the voltage at the first source/drain terminal 601a is fixed at the supply voltage 604. The output current $I_{out}$ is detected by means of the ammeter 603. It should be noted that the capacitance C 606 does not have to be subjected to charge reversal since the voltage is kept constant.

A description is given below, referring to FIG. 7, of an evaluation unit 700 in accordance with a preferred exemplary embodiment of the invention.

The evaluation unit has the functionality of keeping constant the electrical voltage on a sensor line and of simultaneously converting the detected sensor current (preferably linearly) into a sensor voltage. This enables further processing in the voltage domain.

For some applications it may be advantageous for a detected electric sensor current to be converted into a voltage signal. The evaluation unit 700 shown in FIG. 7 shows an exemplary embodiment that enables a current signal $\Delta I_{meas}$ to be converted into a voltage signal $\Delta V_{out}$. The circuit shown in FIG. 7 is used both to keep constant the electrical voltage on the line and to convert the modulated current $I_{meas}$ into a modulated output voltage $V_{out}=I_{meas}Z$. In this case, Z denotes the value of an impedance 701.

As shown in FIG. 7, the modulated value of the electric current $\Delta I_{meas}$ is provided as sensor signal at an input 702 of the evaluation unit 700. The evaluation unit 700 has an operational amplifier 703. The operational amplifier 703 has an inverting input 703a, at which the sensor signal $\Delta I_{meas}$ is provided. Furthermore, the operational amplifier 703 has a noninverting input 703b, to which a constant electrical reference potential $V_{kal}$ is applied. The characteristic electrical voltage $\Delta V_{out}$ is provided at an output 703c of the operational amplifier 703. The output 703c of the operational amplifier 703 is fed back to the inverting input 703a of the operational amplifier 703 via the impedance Z 701. As is furthermore shown in FIG. 7, the electrical potential $V_{kal}$ at the noninverting input 703b of the operational amplifier 703 is provided by means of the constant-voltage source 704. The constant-voltage source 704 is connected between the electrical ground potential 605 and the noninverting input 703b of the operational amplifier 703.

A description is given below, referring to FIG. 8, of a sensor arrangement 800 in accordance with a first preferred exemplary embodiment of the invention.

The sensor arrangement 800 has a multiplicity of sensor devices 801 which are arranged in matrix form and are connected up by means of row and column lines in such a way that the sensor devices 801 can be driven individually or column by column.

The sensor devices 801 of the sensor arrangement 800 are formed on and in a silicon substrate (not shown). In other words, the sensor arrangement 800 is realized as an integrated circuit.

Although the sensor arrangement 800 has a multiplicity of sensor devices 801, only the n-th and (n+1)-th column of sensor devices 801 and also the m-th and (m+1)-th row of sensor devices 801 are shown in FIG. 8 for the purpose of a simplified illustration.

The construction of the sensor device 801 arranged in the n-th column and the m-th row from FIG. 8 is described in more detail by way of example below.

A sensor element 801 of the sensor arrangement 800 is shown schematically as voltage source 802 in FIG. 8, said sensor element being arranged between the ground potential 605 and one terminal of a capacitor 803. The capacitor 803 symbolizes a dielectric which is applied on the sensor element and spatially decouples electrically charged particles to be detected that are situated thereon from the gate region 804c of a detection transistor 804. The other terminal of the capacitor 803 is furthermore coupled to the first source/drain terminal 805a of a calibration transistor 805. The second source/drain terminal 805b of the calibration transistor 805 is coupled to the first source/drain terminal 804a of the detection transistor 804. Furthermore, the first source/drain terminal 804a of the detection transistor 804 is coupled to the first source/drain terminal 806a of a selection transistor 806. The second source/drain terminal 806b of the selection transistor 806 is coupled to a changeover element 807, which is provided jointly for each row of sensor devices 801. The gate terminal 806c of the selection transistor 806 is coupled to a first column line 808, which is provided jointly for each column of sensor devices 801. The second source/drain terminal 804b of the detection transistor 804 is coupled to a row line 809, which is provided jointly for each row of sensor devices 801. The changeover element 807 can be switched in one of two switch positions "a" and "b", depending on whether a calibration mode or a measurement mode is to be set. In accordance with the scenario shown in FIG. 8, the switch element 807 is in the position "b", so that the second source/drain terminal 806b of the selection transistor 806 is coupled to a calibration constant-current source 810. By contrast, if the changeover element 807 is in the switch position "a" (not shown in the figure), then the second source/drain terminal 806b of the selection transistor 806 is coupled to a detection constant-voltage source 811. The value of the electric current flowing on the row line 809 can be detected by means of a current detection unit 812, i.e. an ammeter for example.

Furthermore, a selection terminal 813 is coupled to the first column line 808. If an electrical signal having a logic value "1" is applied to the selection terminal 813, then all the selection transistors 806 of the associated column of sensor devices 801 are electrically conductive, so that the associated column of sensor devices 801c is selected. Furthermore, a calibration terminal 814 is in each case coupled to a respective second column line 815, a common second column line 815 and a common calibration terminal 814 being provided for each column of sensor devices 801. If a signal having a logic value "1" is present at the calibration terminal 814, then all the calibration transistors 805 of the associated column of sensor devices 801 are electrically conductive, thereby enabling calibration.

The functionality of the sensor arrangement 800 is described in more detail below.

Firstly, a description is given of how the sensor devices 801 are calibrated column by column in order to compensate for fluctuating properties between different sensor devices (for example fluctuations in the value of the threshold voltage of the detection transistors 804). In order to calibrate the n-th column, the latter is activated as sole column by a control signal having a logic value "1" being applied to the selection terminal 813 of the n-th column of sensor devices 801. A signal having a logic value "0" is present at the selection terminals 813 of all the other columns of sensor devices 801. As a result, the channel regions of all the selection transistors 806 of the n-th column of sensor devices 801 are electrically conductive, whereas the selection transistors 806 of all the other columns of sensor devices 801 are nonconductive. A read-out or calibration circuit with the changeover element 807 is in each case situated outside each row of sensor devices 801. In order to carry out the calibration, the switch is brought to the position "b". This scenario is shown in FIG. 8. For calibration, a signal having a logic value "1" is momentarily applied to the calibration terminal 814 of the n-th column of sensor devices 801, so that the calibration constant-current source 810 is coupled to the gate terminal 804c of the detection transistor 804 via the conductive selection transistor 806 and the conductive calibration transistor 805. As a result, a constant current $I_{kal}$ is impressed into the sensor device 801. If the calibration transistor 805 is in the on state, then exactly the electrical voltage required to derive the electric current $I_{kal}$ through the detection transistor 804 is established at the gate terminal 804c of the detection transistor 804. This voltage is different for each sensor device 801 of the n-th column of sensor devices 801 since the electrical parameters of the detection transistor 804 may vary on account of statistical effects. If the coupling of the gate terminal 804c and the first source/drain terminal 804a of the detection transistor 804 via the calibration transistor 805 is interrupted again by the signal at the calibration terminal 814 being brought to a logic value "0", clearly the electrical gate voltage associated with the electric current value $I_{kal}$ is stored at the gate terminal 804c of the detection transistor 804. This calibration method is gradually repeated for all the columns.

A measurement phase of the sensor arrangement 800 is described below. For this purpose, the changeover element 807 is switched to the switch position "a". As a result, the constant voltage $V_{drain}$ is impressed into all the circuit devices 801 of an associated row of circuit devices 801 using the detection constant-voltage source 811. The sensor arrangement 800 is sequentially read column by column. A column to be read is selected by the associated selection terminal 813 being brought to an electrical potential with a logic value "1" so that all the selection transistors 806 of the associated column of sensor arrangements 801 are brought to an electrically conductive state. If no sensor event takes place at a sensor element of a sensor device 801 of a selected column of sensor devices 801, then that DC component that was stored on the gate terminal 804c of the detection transistor 804 in the calibration phase flows through the activated sensor device 801. Parameter fluctuations, in particular of the detection transistors 804, are therefore compensated for. In other words, the output signal for an identical sensor event is identical and does not depend on the fluctuating parameters of the transistors. If a sensor event gives rise to a modulation of the electrical potential on a sensor element, then this results in a modulation of the electrical voltage at the gate terminal 804c of the associated detection transistor 804 and consequently of the electric current at the first source/drain terminal 804a of the detection transistor 804. This modulation is detected by means of the current detection unit 812 and can be amplified by external amplifier elements. The electric sensor current signal may optionally be converted into an electrical voltage (cf. evaluation unit 700 from FIG. 7).

To summarize, it shall be emphasized that the sensor devices 801 can be activated and deactivated column by column by means of the sensor arrangement 800. A sensor signal is amplified or converted into an electric current. Statistical fluctuations of parameters of the sensor devices 801 are compensated for by means of calibrating the sensor devices 801.

A description is given below, referring to FIG. 9, of a sensor arrangement 900 in accordance with a second preferred exemplary embodiment of the invention. The sensor arrangement 900 shown in FIG. 9 is a modification of the sensor arrangement 800 shown in FIG. 8. Identical or similar components are therefore provided with the same reference numerals.

The essential difference between the sensor arrangement 900 and the sensor arrangement 800 is that the calibration transistor 805 is connected up in a modified manner in the case of the sensor devices 901 of the sensor arrangement 900.

In the case of the sensor arrangement 900, the second source/drain terminal 805b of the calibration transistor 805 is coupled to the second source/drain terminal 806b of the selection transistor 806 and directly to the row line 809. By virtue of the calibration transistor 805 of the sensor arrangement 900 being directly coupled to the row line 809 (clearly readout line), it is possible to compensate for slight fluctuations which may arise via the selection transistor 806. However, the parasitic capacitance at the output node of a sensor arrangement 901 in accordance with the sensor arrangement 900 may be somewhat higher since, in this case, two transistors are permanently connected by their source/drain terminals to the common output node of a sensor arrangement 901 of a row.

A description is given below, referring to FIG. 10, of a sensor arrangement 1000 in accordance with a third preferred exemplary embodiment of the invention. Those components of the sensor arrangement 1000 which also occur in the sensor arrangement 800 or 900 are provided with the same reference numerals.

The sensor arrangement 1000 is a matrix-type arrangement of a multiplicity of sensor devices 1005.

A sensor element of a sensor device 1005 is again symbolized as voltage source 802, which, in accordance with FIG. 10, are connected between a terminal at electrical ground potential and the capacitor 803. The capacitor 803 represents a dielectric layer on the detection transistor 804, by means of which the sensor element 802 is decoupled from the detection transistor 804. The capacitor 803 is coupled to the first source/drain terminal 1001a of a switching transistor 1001. The second source/drain terminal 1001b of the switching transistor 1001 is coupled to the first source/drain terminal 805a of the calibration transistor 805 and to the gate terminal 804c of the detection transistor 804. Furthermore, the gate terminal 1001c of the switching transistor 1001 is coupled to a switching terminal 1002 via a third column line 1003. A separate third column line 1003 is provided for each column of sensor devices 1005. The first source/drain terminal 804a of the detection transistor 804 is coupled to the first source/drain terminal 806a of the selection transistor 806, the gate terminal 806b of which is coupled to the selection terminal 813 via the first column line 808. The gate terminal 805c of the calibration transistor 805 is coupled to the calibration terminal 814 via the second column line 815. The second source/drain terminal 805b of the calibration transistor 805 is coupled to a first row line 1006, which is provided jointly for each row of sensor devices 1005. The first row line 1006 is coupled to a calibration constant-voltage source 1004. The second source/drain terminal 806b of the selection transistor 806 is coupled via a second row line 1007 to the detection constant-voltage source 811, which is in turn coupled to the current detection unit 812. The current detection unit 812 is coupled to the calibration constant-voltage source 1004.

The functionality of the sensor arrangement 1000 is described in more detail below.

In the case of the sensor arrangement 1000, the sensor devices 1005 can be activated and deactivated column by column. The sensor signal or a reference signal can be amplified or converted into an electric current. Furthermore, the sensor device 1000 is suitable for a correlated double sampling for the purpose of eliminating parameter fluctuations.

It should be noted that the n-MOS transistors 1001, 805, 806 coupled to one of the column lines 1003, 815 and 808, respectively, can be brought to an electrically conductive state by application of an electrical signal having a logic value "1" to the associated terminal 1002, 814 and 813, respectively, and thus represent a negligibly small nonreactive resistance. By contrast, if the electrical signal at an associated terminal 1002, 814 and 813, respectively, is at a logic value "0", then the driven transistor is in the off state, in which case the leakage currents of the field-effect transistors can be disregarded.

The sensor arrangement 1000 is based on the correlated double sampling principle (CDS), whereby parameter fluctuations and low-frequency noise are suppressed. In accordance with the CDS method, it is customary firstly to apply a reference signal to an input of an amplifier. The amplified reference signal plus an offset signal of the amplifier is then stored at the output of the amplifier. In a next phase, the sensor signal is applied to the amplifier. The amplified measurement signal including the offset signal is then present at the output of the amplifier. Forming the difference between the two values makes it possible to eliminate the offset signal of the amplifier.

The sensor devices 1005 of the sensor arrangement 1000 are sequentially read column by column. A column (e.g. the n-th column) of sensor devices 1005 is in each case activated by the selection terminal 813, the first column line 808 and consequently the gate terminal 806c of the selection transistors 806 of the associated column being brought to a logic value "1". The pixels of a column are read in two phases in accordance with the exemplary embodiment.

In a first phase, the reference voltage $V_{kal}$ of the calibration constant-voltage source 1004, in an associated sensor arrangement 1005, is converted into an electric current and the value thereof is detected. For this purpose, an electrical signal having a logic value "1" is applied to the calibration terminal 814, so that the calibration transistors 805 coupled thereto via the second column line 815 are brought to an electrically conductive state. By contrast, the switching terminal 1002 is at a logic value "0" in this phase, so that the switching transistor 1001 is electrically nonconductive. The reference voltage $V_{kal}$ is present at the gate terminal 804c of the detection transistor 804, which results in an associated electric current through the first source/drain terminal 804a of the detection transistor 804. The value of said electric current may be different for different sensor devices 1005 of the sensor arrangement 1000 on account of statistic fluctuations of transistor parameters. The value of said electric current is detected and stored in the read-out circuit of the respective row as electric reference current $I_{meas}(m)$.

The actual sensor signal is detected in a second phase. In a shortest possible time interval with respect to the first phase, the electrical signal at the calibration terminal 814 is brought to a logic value "0" as a result of which the calibration transistors 805 turn off. By contrast, an electrical signal having a logic value "1" is applied to the switching terminal 1002, so that the switching transistors 1001 are brought to an electrically conductive state. As a result, a change in the electrical potential at the sensor element 802 is mapped on the gate terminal 804c of the detection transistor 804, which leads to a modulation of the electric current through the first source/drain terminal 804a of the detection transistor 804. The value of said electric current is detected, and the difference between the detected current values from the first and the second phase is then formed. As a result, parameter fluctuations between the different sensor devices are suppressed and the output signal obtained depends exclusively on the sensor event.

LIST OF REFERENCE SYMBOLS

100 Sensor arrangement
101 First sensor device
102 Second sensor device
103 Third sensor device
104 Fourth sensor device
105 Multiplexer
106 Read-out circuit
200 Sensor arrangement
201 Nonreactive resistance
202 Capacitance
300 Diagram
301 Abscissa
302 Ordinate
303 Signal profile curve
400 Output driver circuit
401 MOS transistor
402 Voltage source
403 Constant-current source
404 Nonreactive resistance
405 Capacitance
406 Supply voltage
407 Ground potential
410 Equivalent circuit diagram
411 Controlled current source
412 Internal resistance
500 Output driver circuit
510 Equivalent circuit diagram
511 Controlled current source
512 Internal resistance
600 Sensor device
601 Field-effect transistor
601a First source/drain terminal
601b Second source/drain terminal
601c Gate terminal
602 Voltage source
603 Ammeter
604 Supply voltage
605 Ground potential
606 Capacitor
700 Evaluation unit
701 Impedance
702 Input
703 Operational amplifier
703a Inverting input
703b Noninverting input
703c Output
704 Constant-voltage source
800 Sensor arrangement
801 Sensor device
802 Voltage source
803 Capacitor
804 Detection transistor 804a First source/drain terminal
804b Second source/drain terminal
804c Gate terminal
805 Calibration transistor
805a First source/drain terminal
805b Second source/drain terminal
805c Gate terminal
806 Selection transistor
806a First source/drain terminal
806b Second source/drain terminal
806c Gate terminal
807 Changeover element
808 First column line
809 Row line
810 Calibration constant-current source
811 Detection constant-voltage source
812 Current detection unit
813 Selection terminal
814 Calibration terminal
815 Second column line
900 Sensor arrangement
901 Sensor device
1000 Sensor arrangement
1001 Switching transistor
1001a first source/drain terminal
1001b Second source/drain terminal
1001c Gate terminal
1002 Switching terminal
1003 Third column line
1004 Calibration constant-voltage source
1005 Sensor device
1006 First row line
1007 second row line

The invention claimed is:

1. A sensor arrangement having a plurality of sensor devices formed at least one of on or in a substrate, each of the sensor devices having:
   an electrical signal converter;
   a sensor element coupled to the signal converter, in which the sensor element can be used to characteristically influence the electrical conductivity of the signal converter on account of a sensor event on the sensor element;
   a device for keeping constant an electrical voltage present at the signal converter; and
   a device for detecting the value of the electric current flowing through the signal converter as a sensor signal,
   wherein the electrical signal converter is a field-effect transistor having a gate terminal coupled to the sensor element, the device for keeping constant an electrical voltage keeps constant the electrical voltage between source and drain terminals of the field-effect transistor; and
   the sensor arrangement further comprises a calibration device for calibrating a respective sensor device, the calibration device usable to bring a gate region of the field-effect transistor to an electrical calibration potential such that the electric current is independent of parameter fluctuations of the field-effect transistor.

2. The sensor arrangement as claimed in claim 1, further comprising an evaluation unit, which is provided with the value of the electric current as sensor signal.

3. The sensor arrangement as claimed in claim 2, in which the evaluation unit forms, from the value of the electric current, an electrical voltage characteristic of the value or maps the value of the electric current onto a digitally coded value that characterizes the value of the electric current.

4. The sensor arrangement as claimed in claim 3, in which the evaluation unit has an operational amplifier comprising:
   a first input, to which the sensor signal can be applied;
   a second input, to which an electrical reference potential can be applied; and
   an output, at which the characteristic electrical voltage is provided;
   the first input and the output being coupled to one another by means of a nonreactive resistor.

5. The sensor arrangement as claimed in claim 1, configured as a biosensor arrangement.

6. The sensor arrangement as claimed in claim 1, in which the calibration device is set up such that an electric calibration current can be applied to the gate terminal and to one of the source and drain terminal of the field-effect transistor for calibration purposes.

7. The sensor arrangement as claimed in claim 2, in which the evaluation unit has a correlated double sampling device, which forms, in the case of a sensor event, a value of the electric current that is independent of parameter fluctuations of the field-effect transistor.

8. The sensor arrangement as claimed in claim 7, in which the correlated double sampling device is set up such that, by means of the correlated double sampling device:
   in a calibration phase, a gate region of the field-effect transistor is brought to an electrical calibration potential and the associated value of the electric current is detected as a calibration signal and stored;
   in a detection phase, the value of the electric current on account of a sensor event is detected as a sensor signal;
   in an evaluation phase, the sensor signal and the calibration signal are evaluated jointly.

9. The sensor arrangement as claimed in claim 1, in which the sensor devices are arranged essentially in matrix form at least one of on or in the substrate and are connected up by means of row and column lines such that the sensor devices can be driven individually, row by row or column by column.

10. The sensor arrangement as claimed in claim 9, in which at least one evaluation unit, at least one of: at least one calibration device or at least one correlated double sampling device is provided jointly for at least a portion of the sensor devices of a row line or a column line.

11. A method for operating a sensor arrangement:
   with a sensor arrangement having a plurality of sensor devices formed at least one of on or in a substrate, each of the sensor devices having:
   an electrical signal converter;
   a sensor element coupled to the signal converter, in which the sensor element can be used to characteristically influence the electrical conductivity of the signal converter on account of a sensor event on the sensor element;
   a device for keeping constant an electrical voltage present at the signal converter;
   a device for detecting the value of the electric current flowing through the signal converter as a sensor signal, wherein the electrical signal converter is a field effect transistor having a gate terminal coupled to the sensor element, the device for keeping constant an electrical voltage keeps constant the electrical voltage between source and drain terminals of the field-effect transistor;
   in which case, in accordance with the method,
   the electrical conductivity of the signal converter is characteristically influenced on account of a sensor event on the sensor element;

the electrical voltage at the signal converter is kept constant;

the electric current flowing through the signal converter is detected as sensor signal; and in which at least a portion of the sensor devices is calibrated by a gate region of the respective field-effect transistor being brought to an electrical calibration potential such that the value of the electric current in the case of a sensor event is independent of parameter fluctuations of the field-effect transistor.

12. The method as claimed in claim 11, in which a value of the electric current that is independent of parameter fluctuations of the field-effect transistor is formed using a correlated double sampling method in the case of a sensor event.

* * * * *